(12) United States Patent
Barber

(10) Patent No.: US 6,266,864 B1
(45) Date of Patent: *Jul. 31, 2001

(54) METHOD FOR FABRICATING A NEEDLE ASSEMBLY

(75) Inventor: Brian Barber, Grand Prairie, TX (US)

(73) Assignee: Ethicon, Inc., Somerville, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/384,709

(22) Filed: Aug. 26, 1999

(51) Int. Cl.$^7$ .............................. B21D 39/03; A24F 15/04
(52) U.S. Cl. ............................................. 29/428; 221/254
(58) Field of Search ...................... 29/407.07, 428, 29/407.01; 221/254, 258, 278

(56) References Cited

U.S. PATENT DOCUMENTS

| | | | | |
|---|---|---|---|---|
| 1,159,195 | * | 11/1915 | Eden | 221/254 |
| 1,457,050 | * | 5/1923 | Abbaticchio | 221/254 |
| 1,498,476 | * | 6/1924 | Nadwocki | 221/254 |
| 1,696,787 | * | 12/1928 | Zelkowitz et al. | 221/254 |
| 2,346,863 | * | 4/1944 | Pacione | 221/254 |
| 2,541,945 | * | 2/1951 | Smith | 221/254 |
| 4,375,854 | * | 3/1983 | Hedel | 221/254 |
| 4,480,765 | * | 11/1984 | Tonus | 221/254 |
| 4,809,882 | * | 3/1989 | Neu | 221/254 |
| 5,067,631 | * | 11/1991 | Baba | 221/254 |

* cited by examiner

Primary Examiner—S. Thomas Hughes
Assistant Examiner—Marc Jimenez
(74) Attorney, Agent, or Firm—Blakely, Sokoloff, Taylor & Zafman

(57) ABSTRACT

Methods and apparatuses for fabricating a needle assembly which includes a blunt in a cannula of a needle. In one example of a method, at least one blunt is collected in a cutout of a blade from a set of blunts and a fluid is passed across said cutout. Any further blunts around the cutout are dislodged by the fluid, leaving only one blunt on the blade. In another example of a method, a blade is moved to a first position to collect at least one blunt from a set of blunts, and the blade is moved to a second position to singulate the one blunt from the set of blunts; the blade has a tip end which is designed to capture securely only one blunt, wherein any further blunts are not securely maintained in the tip end. An exemplary apparatus includes a container for holding a set of blunts, a motor, and a blade coupled to the motor and disposed at least partially within a slot of said container. The blade includes a tip end which is designed to capture securely only one blunt.

10 Claims, 6 Drawing Sheets

METHOD FOR FABRICATING A NEEDLE ASSEMBLY

BACKGROUND OF THE INVENTION

The present invention relates to methods and apparatuses for fabricating an assembly which includes a blunt and, in one particular embodiment, relates to an apparatus for fabricating a needle assembly which includes a blunt.

The present invention relates to medical devices and other similar devices and in particular to medical devices such as intravenous catheters and syringes which include a hollow needle having a sharp distal end for piercing an object, such as the skin of a patient.

The existence of infectious diseases has highlighted the danger to which medical personnel may be exposed when treating patients by means of catheter devices and syringes where a sharp needle point is used to pierce the skin of the patient. In order to protect medical personnel against inadvertent needle stick, a number of solutions have been developed whereby a protective mechanism, incorporated within a catheter or syringe, prevents physical contact with the sharp needle point after use and hence protects against inadvertent needle stick. One such solution which has been developed is the use of a blunt which is contained within the cannula of the hollow needle. An example of a blunt is described in co-pending U.S. patent application Ser. No. 09/221,272, which was filed Dec. 23, 1998, by the inventors Joseph, Chang, Philip Schmidt, and Dennis Bialecki and which is entitled "Solid Blunt for a Needle Assembly." One example of a blunt described in this patent application is a blunt having a substantially D-shaped cross-section. In mass production, this blunt would typically be manufactured in large numbers before being inserted into the cannula of a needle in order to create the final product. Current manufacturing techniques for producing needle assemblies often include the use of a blade-style feeder which singulates a needle from a collection of needles in order to assemble the needle with the rest of the assembly which makes up the needle assembly. FIG. 1 shows an example of a process for singulating a needle from a collection of needles in order to fabricate a needle assembly by connecting the needle to a hub, etc. The feeder 101 is shown in FIG. 1 in cross-sectional view. The feeder includes a container 103 which has a wall 109 which supports a plurality of needles 107 such as needles 107a, 107b, 107c, and 107d. A blade-style feeder 105 is disposed within a slot 111 of the container 103. The blade 105 is coupled to a motor 112 which drives the blade up and down as shown by the arrow 114. When the blade 105 is driven down such that the top surface of the tip 105a is approximately at the position 105b as shown in FIG. 1, then one needle will tumble into the cutout of the tip 105a. As the blade 105 is pushed up away from the wall 109 to the position shown in FIG. 1, only one needle will remain in the tip 105a as any other needles will tumble off of the top of the tip 105a. This causes a single needle to be selected in a singulation process from the set of needles held in the container 103.

It is desirable in the manufacturing process for needle assemblies which include blunts to use a similar blade-style feeder to singulate a blunt from a set of blunts in order to take the singulated blunt and then insert it into the cannula of a needle to assemble the needle assembly. A D-shaped blunt presents a challenge for the blade-style feeder shown in FIG. 1. This challenge is shown in FIGS. 2A and 2B which show that the blade 105 may not successfully singulate one blunt from a collection of blunts. As shown in FIG. 2A, which is a cross-sectional view, two D-shaped blunts 203 and 205 may be stably maintained on the cutout of the tip 105a. In this case, it may be impossible to singulate one blunt from a group of blunts. Similarly, as shown in FIG. 2B which is a cross-sectional view, two blunts 207 and 209 may remain stably held in the cutout of the tip 105a when the blunts stack vertically as shown in FIG. 2B.

While it is desirable to use a feeder to singulate blunts in the same manner that a feeder is used to singulate needles, the currently existing blades do not provide adequate performance in singulating blunts.

From the above discussion, it can be seen that it is desirable to provide an improved method and apparatus for singulating a blunt in the process of fabricating a needle assembly or for fabricating other assemblies which use a blunt.

SUMMARY OF THE INVENTION

The present invention provides a method of fabricating an assembly which includes a blunt, and also provides an apparatus for fabricating an assembly which includes a blunt.

In one exemplary embodiment, a method of the invention includes collecting from a set of blunts at least one blunt in a blade having a cutout and passing a fluid past the cutout. In another example according to the present invention, the method includes moving a blade to a first position to collect at least one blunt from a set of blunts and moving the blade to a second position to singulate the one blunt from the set of blunts, where the blade has a tip end which is designed to capture securely only the one blunt and wherein any further blunts are not securely maintained in the tip end.

An apparatus in another exemplary embodiment includes a container for holding a set of blunts and includes a motor. A blade, which is disposed at least partially within a slot of the container and which is coupled to the motor, has a tip end which is designed to capture securely only one blunt, wherein any further blunts are not securely maintained in the tip end.

The present invention may be used to fabricate medical devices, including needles, syringes, catheter assemblies and introducers for catheters as well as other devices which include a blunt.

BRIEF DESCRIPTION OF THE DRAWINGS

The present invention is illustrated by way of example and not limitation in the figures of the accompanying drawings in which like references indicate similar elements.

DETAILED DESCRIPTION

The present invention provides various examples of methods and apparatuses for fabricating an assembly which includes a blunt. The following description and drawings are illustrative of the invention and are not to be construed as limiting the invention. Numerous specific details are described to provide a thorough understanding of the invention. For example, very specific geometries and dimensions are provided for purposes of illustrating the invention. In certain instances, well known or conventional details are not described in order to not unnecessarily obscure the present invention in detail.

Figure 1:
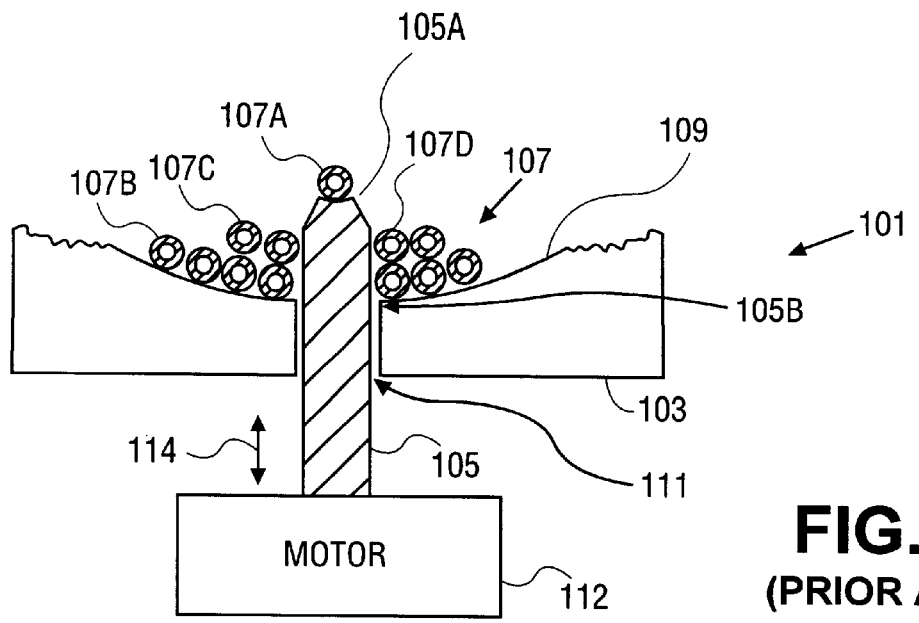
FIG. 1 shows a cross-sectional view of a prior art system for singulating one hollow needle shaft from a group of hollow needle shafts.
Figure 2A:
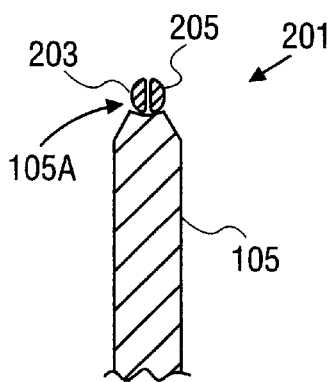
FIG. 2A shows an example of the use of the blade-style feeder from FIG. 1 in a system which is attempting to singulate a D-shaped blunt.
Figure 2B:
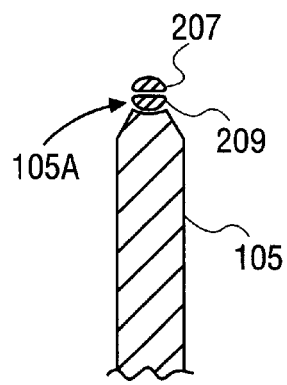
FIG. 2B shows another example of the blade-style feeder from FIG. 1 and its attempt to singulate two D-shaped blunts.
Figure 3:
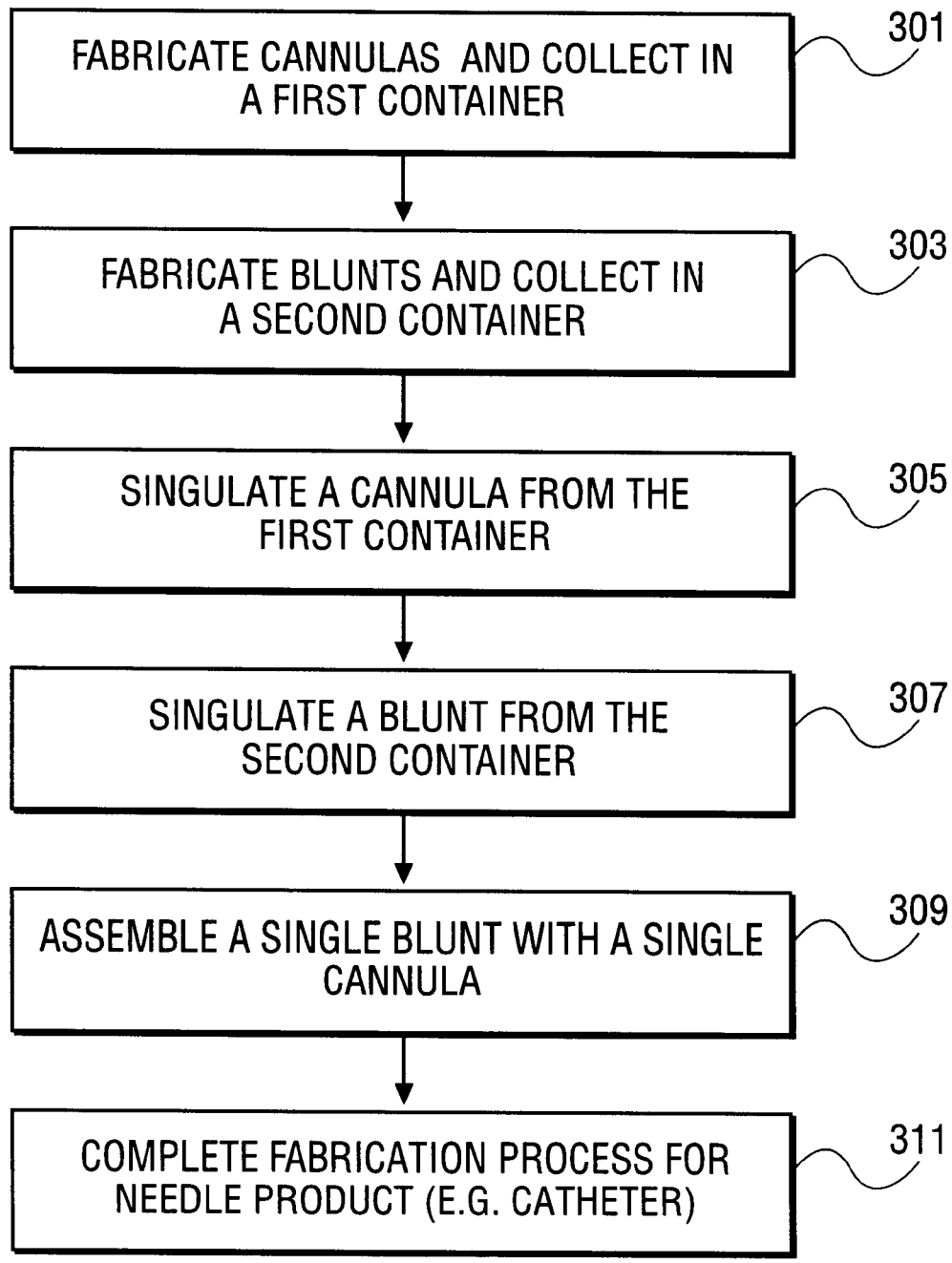
FIG. 3 is a flowchart which shows a sequence of operations in a manufacturing process for assembling a blunt into the cannula of a needle in order to fabricate a medical device such as a syringe or a catheter introducer.

At least one embodiment of the present invention allows the utilization of familiar feeding technology in order to singulate both the needles and the blunts to provide a single needle which then may be mated with a single blunt. This is particularly desirable when the manufacturing assembly process requires that the D-shaped blunt in one embodiment be singulated before being bonded to the needle's hub or other components in the assembly. FIG. 3 shows an example of the flow of operations in a manufacturing assembly process according to one embodiment of the invention. Operation 301 involves the fabrication of the needles (referred to as cannulas here). The needles are collected on a first container. In operation 303, the blunts are fabricated and collected in a second container. Then in operation 305, a single needle is selected from the collection of needles in the first container. Similarly, in operation 307, a single blunt is selected from the collection of blunts in the second container. Then in operation 309, the single blunt singulated in operation 307 is assembled with the single needle singulated in operation 305. In operation 311, the fabrication process is completed to complete the final product, such as a catheter introducer or a syringe. It will be appreciated that several of the steps may be performed in a different order or concurrently. However, it is desirable in this embodiment to singulate the needle and the blunt prior to their assembly in operation 309. The present invention provides, in at least one embodiment, a method and apparatus for singulating a blunt which has a D-shaped geometry or other geometries which may make it difficult to singulate a blunt from a group of blunts.

Figure 4A:
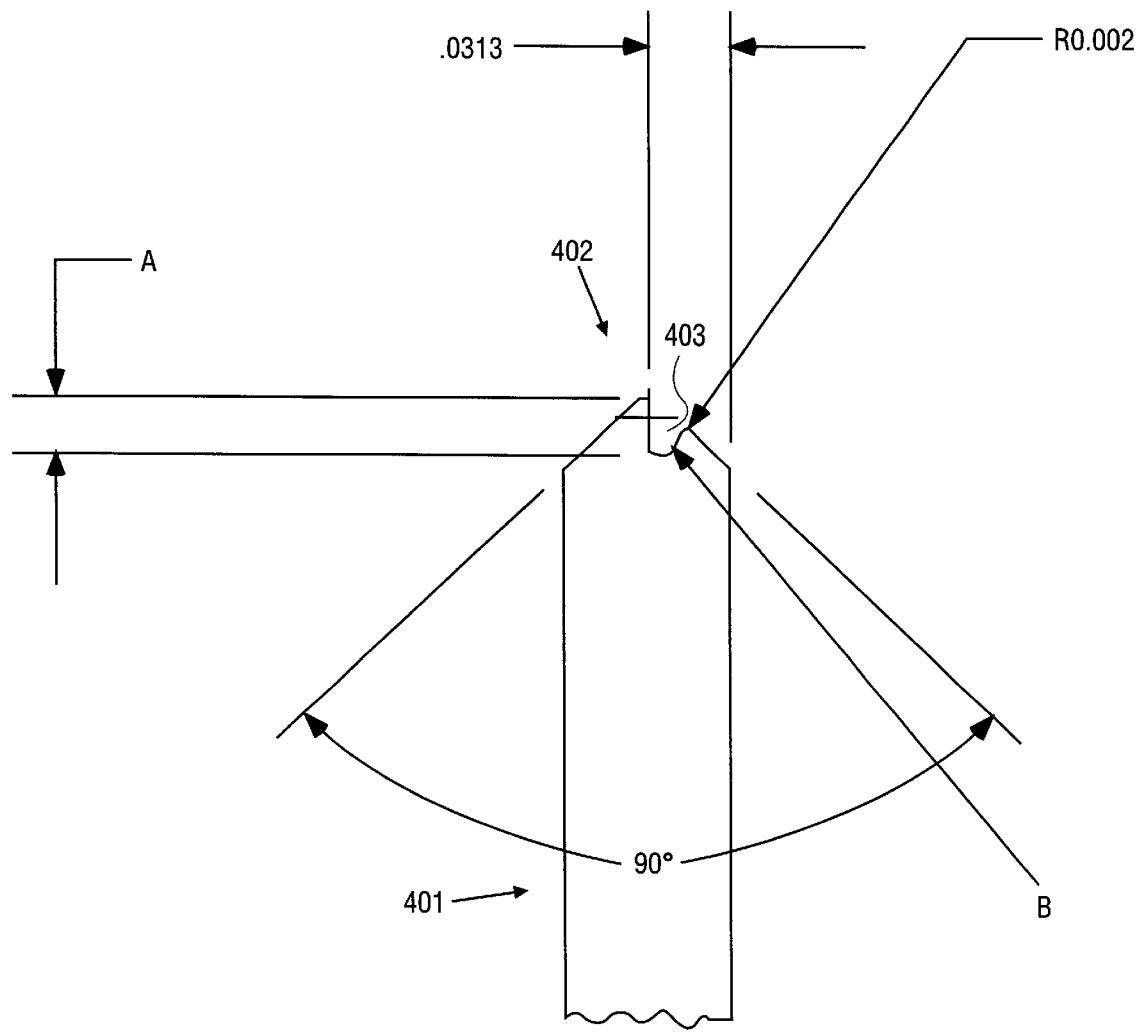
FIG. 4A shows a cross-sectional view of a blade feeder according to one embodiment of the present invention.

FIG. 4A shows a cross-sectional view of one example of a blade feeder of the present invention. In this cross-sectional view, the blade 401 includes a main body which has a tip end 402 which includes a cutout 403. The cutout 403 is designed to have a geometry, relative to the geometry of the cross-section of the blunt, so that only one blunt is securely maintained in the cutout and any further blunts will not be securely maintained within the cutout. FIG. 4A shows various dimensions and angles for a particular embodiment of a blade feeder of the invention. This figure and the following table provide very specific examples for dimensions of certain feeders. In particular, in Table A below, specific examples for particular dimensions of the feeder are specified relative to certain D-shaped blunts of specified gauge sizes. The dimension A shown in FIG. 4A corresponds to A in the table, and the dimension B shown in Table A corresponds to the dimension B shown in FIG. 4A. The dimensions shown in FIG. 4A are in inches.

TABLE A

| Gauge Size | Dim "A" ± .001 | Dim "B" ± .001 |
| --- | --- | --- |
| 14 gauge | .050 | .034 |
| 16 gauge | .037 | .026 |
| 18 gauge | .030 | .020 |
| 20 gauge | .022 | .015 |
| 22 gauge | .016 | .011 |
| 24 gauge | .013 | .009 |

The gauge size in Table A represents the gauge size of the D-shaped blunt. It can be seen that in this particular embodiment, the geometry of the tip end of the blade consists of a quarter-pie-shaped profile where one portion of the profile is higher than the other. This higher portion of the profile provides protection for a single blunt from an air jet which is used in one embodiment as described below. The dimensions shown in the table are in inches.

Figure 4B:
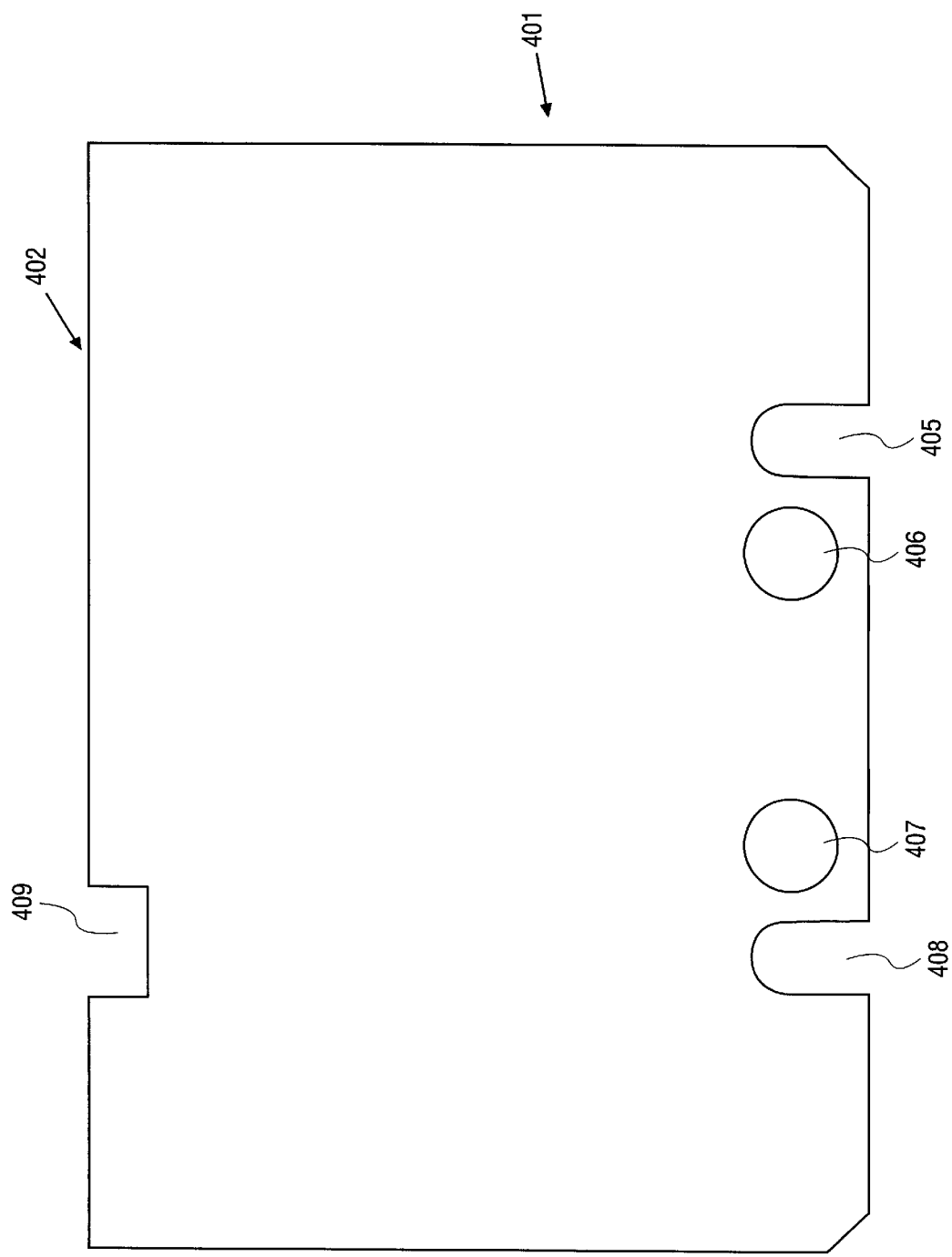
FIG. 4B shows a side view of a blade feeder according to one embodiment of the present invention.

FIG. 4B shows a side view of the blade according to one exemplary embodiment of the invention. The blade 401 includes a tip end 402 and also includes another end where several cutouts 405, 406, 407, and 408 are located. These cutouts may be used to couple the blade to the motor which drives the blade up and down within the assembly, such as the motor 112 of FIG. 5 which will be described below. The tip end also includes a cutout 409. The cutout 409 is used, in conjunction with a gripper, to remove a singulated blunt from the blade.

Figure 5:
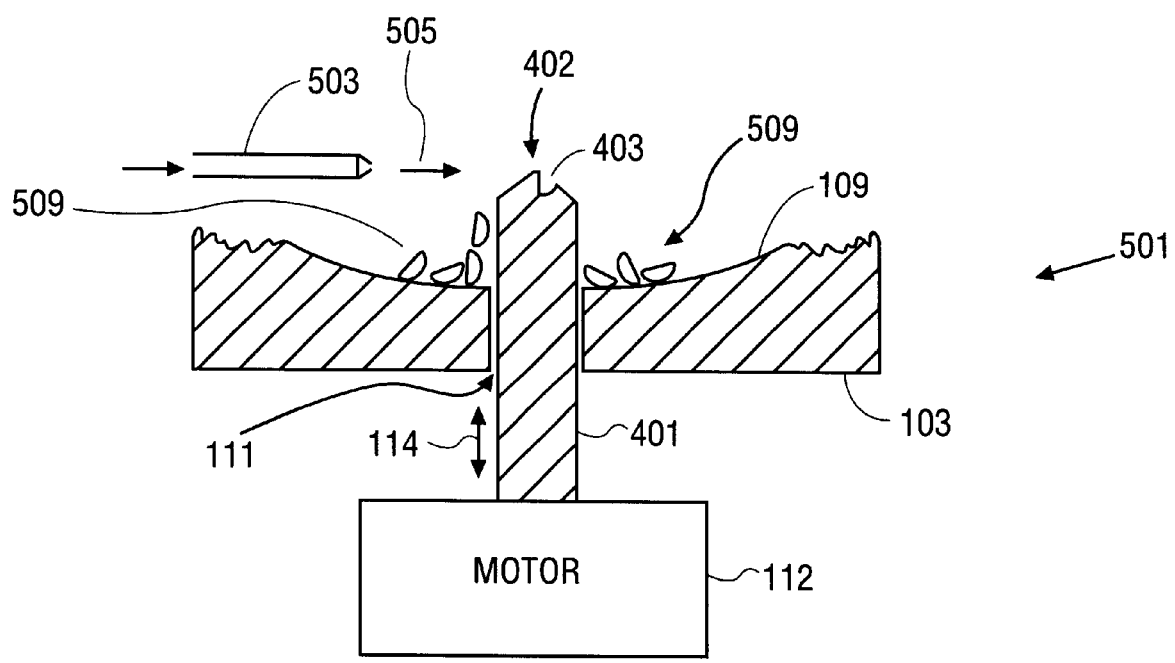
FIG. 5 illustrates the use of a blade according to the present invention in an apparatus according to the present invention which may be used to singulate D-shaped blades.

FIG. 5 shows a cross-sectional view of an apparatus according to one exemplary embodiment of the invention. The apparatus 501 includes a container 103 which holds a collection of blunts along the wall 109 of the container. The collection of blunts 509 will be singulated by the blade 401. The blade 401 is coupled to the motor 112 which causes the blade 401 to move up and down within the slot 111 of the container 103 along the vertical arrow 114 as shown in FIG. 5. The reciprocating up and down motion of the blade 401 causes the blade's cutout 403 to securely select only one D-shaped blunt from the collection of blunts 509.

One particular embodiment of the present invention may utilize a fluid, such as a pressurized air stream, which is pulsed to provide a jet of air when the blade 401 reaches its uppermost position in its travel up and down. The jet of air 505 may be emitted from a nozzle 503 which is positioned to direct the stream of air at approximately the location that the tip 402 will be in when the blade 401 is near its uppermost trajectory in its up and down travel. Alternatively, the air jet may be maintained on a constant on state or the air jet may be turned on when a sensor detects more than one blunt in the blade cutout 403. The sensor may be an automatic sensor such as a light-detecting sensor (e.g. a beam of light is projected across the top of the tip and can only be interrupted when more than one blunt is present in the cutout and when the blade is at its uppermost position).

Figure 6A:
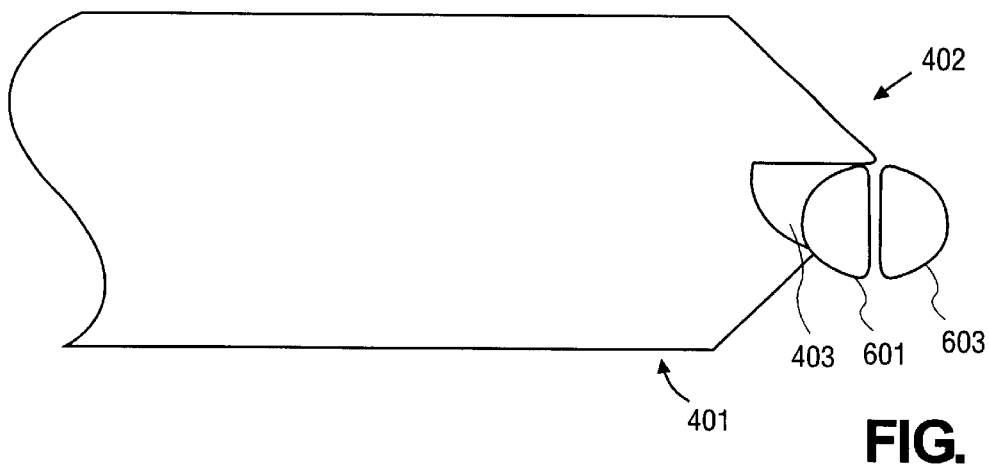
FIGS. 6A, 6B, and 6C are cross-sectional views showing various examples of how the blade of the present invention, according to one embodiment, will successfully singulate a blade from a group of blades.
Figure 6B:
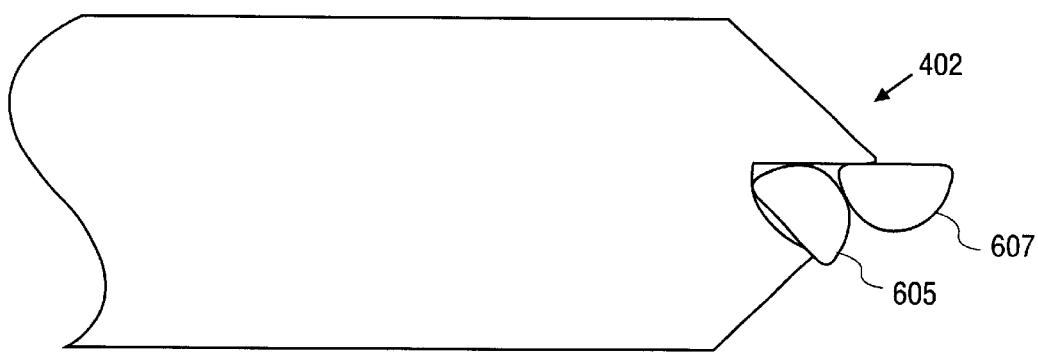
Figure 6C:
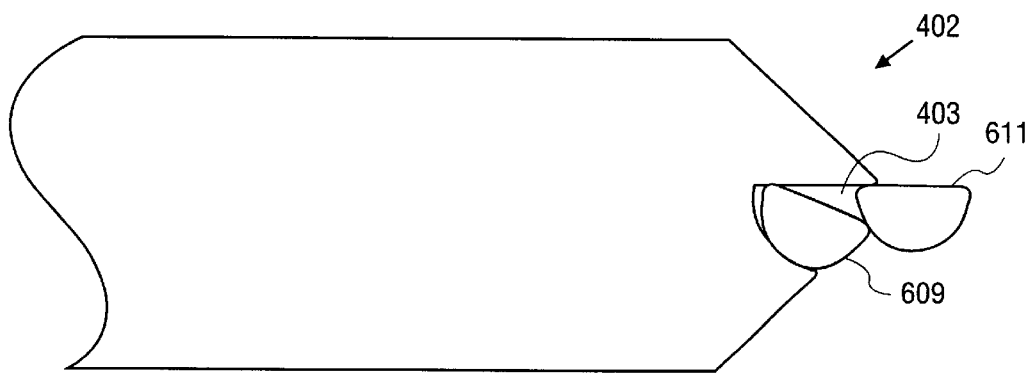

FIGS. 6A, 6B and 6C show various examples of how more than one D-shaped blunt can be picked up by the blade 401 in the cutout 403. However, in each case, the second blunt is significantly exposed and will not be maintained on the tip end of the blunt after the air jet is pulsed to remove the second blunt.

It will be appreciated that other blunt shapes may be accommodated in the blade by altering the shape of the cutout in the tip end of the blade. The shape of the cutout should be designed to securely hold only one blunt and to leave any other blunts not securely maintained so that an air jet, if used, may remove the second blunt. In another alternative embodiment, the blade may be vibrated to knock off an extra blunt.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A method of separating a blunt from a set of blunts useable as part of a process to fabricate an assembly, said method comprising:

fabricating a set of needles;

collecting, from said set of needles, at least one needle;

fabricating said set of blunts;

collecting, from said set of blunts, at least one blunt in a blade having a cutout;

passing a fluid past said cutout to remove all but said at least one blunt from said cutout; and assembling said at least one blunt with said at least one needle.

2. A method as in claim 1 further comprising:

designing said set of blunts to provide needle stick prevention; and designing said set of blunts to extend from beyond a distal end of said needle after said needle is used.

3. A method as in claim 2, said method further comprising:

moving said blade in a predetermined fashion to perform said collecting.

4. A method as in claim 3 further comprising:

configuring said predetermined fashion such that said blade moves in an up and down motion.

5. A method as in claim 4 wherein said method further comprises:

dispensing said set of blunts into a container, and wherein said blade is disposed in a slot in a wall of said container and said blade moves up and down in said slot.

6. A method as in claim 1 further comprising configuring said passing a fluid to include pressurized air which is directed in a stream toward said cutout.

7. A method as in claim 4 further comprising directing said passing a fluid at said cutout when said blade is up.

8. A method as in claim 4 further comprising directing said passing a fluid toward said cutout when more than said at least one blunt is detected in said cutout.

9. A method as in claim 1 further comprising:

mounting said at least one blunt into said at least one needle.

10. A method for separating a blunt from a set of blunts useable as part of a process to fabricate an assembly, said method comprising:

fabricating a set of needles;

collecting, from said set of needles, at least one needle;

fabricating said set of blunts;

moving a blade to a first position to collect at least one blunt from said set of blunts;

moving said blade to a second position to singulate said at least one blunt from said set of blunts, said blade having a tip end which is designed to capture securely only one said blunt at a time, wherein in an event that a further blunt couples to said tip end at said time, said further blunt is not securely maintained in said tip end at said time;

passing a fluid over said tip end, said passing a fluid dislodges said further blunt from said tip end in the event that said further blunt couples to said tip end; and assembling said at least one blunt with said at least one needle.

* * * * *